United States Patent [19]

Haar

[11] Patent Number: 5,413,764
[45] Date of Patent: May 9, 1995

[54] TEST CARRIER ANALYSIS SYSTEM

[75] Inventor: Hans-Peter Haar, Wiesloch, Germany

[73] Assignee: Boehringer Mannheim GmbH, Mannheim, Germany

[21] Appl. No.: 503,585

[22] Filed: Apr. 3, 1990

[30] Foreign Application Priority Data

Apr. 8, 1989 [DE] Germany .......... 39 11 539.9

[51] Int. Cl.⁶ .............................................. G07N 21/75
[52] U.S. Cl. .................. 422/82.09; 422/61; 436/169; 364/551.01; 364/413.11
[58] Field of Search ............... 436/169, 170; 422/55-60, 82.05-82.09, 61, 68.1, 82.01, 82.02; 435/4; 204/403; 364/413.08, 413.11, 497, 551.01

[56] References Cited

U.S. PATENT DOCUMENTS

| | | | |
|---|---|---|---|
| 3,139,328 | 6/1964 | Jacob | 422/56 |
| 4,578,716 | 3/1986 | Rijckevorsel et al. | 360/1 |
| 4,592,893 | 6/1986 | Poppe et al. | 422/56 |
| 4,839,297 | 6/1989 | Frietag et al. | 436/170 |
| 4,852,025 | 7/1989 | Herpichbohm | 364/551.01 |
| 4,877,580 | 10/1989 | Aronowitz et al. | 422/58 |
| 4,935,346 | 6/1990 | Phillips et al. | 435/14 |
| 4,960,565 | 10/1990 | Shurben | 422/61 |
| 4,985,205 | 1/1991 | Fritsche et al. | 422/56 |
| 5,023,052 | 6/1991 | Nagatomo et al. | 422/56 |
| 5,037,614 | 8/1991 | Makita et al. | 422/82.05 |

Primary Examiner—Robert J. Warden
Assistant Examiner—T. A. Trembley
Attorney, Agent, or Firm—Nikaido, Marmelstein, Murray & Oram

[57] ABSTRACT

A test carrier analysis system for analyzing a body fluid, the system including a test carrier (1) with a detection layer (20) on which a detectable change specific to the analysis takes place, obeying an evaluation curve, to the concentration of the component, and wherein the evaluation curve is dependent on the manufacturing batch of the test carrier. The system further includes an evaluator having a measuring and digitization circuit (25) which generates from the physically detectable change an intermediate result independent of the evaluation curve in the form of a finite number of digital output states, and having a display (7) for indicating the output states in the form of an alpha and/or numeric code. A readable information carrier element is provided having a correlation thereon between the alphanumeric codes of the display (7) corresponding to the output states and the concentration values determined in accordance with the evaluation curve.

10 Claims, 2 Drawing Sheets

TEST CARRIER ANALYSIS SYSTEM

FIELD OF THE INVENTION

The invention relates to a test carrier analysis system.

DESCRIPTION OF THE PRIOR ART

Such systems are increasingly used for the analysis of body fluids, in particular urine and blood, for medical purposes. The test carriers usually take the form of test strips or are designed as flat, approximately square platelets. They contain one or more test layers in which reagents are embedded. The latter are brought into contact with the sample, in the testing of urine generally by immersion, while for the testing of blood a drop of blood is usually dripped onto the carrier.

The reaction of the sample with the reagents in the test layers leads to a detectable change in one of the layers, which is termed the detection layer. In most cases an optically detectable change is involved, in particular a color change. However, test carriers based for example on electrochemical principles are also known in which the physically detectable change relates to an electric current or an electric voltage.

The physically detectable change is determined by means of an evaluation instrument, hereinafter termed "evaluator" belonging to the system, which comprises a suitable measuring device, in the cases mentioned a reflection photometer for measuring the diffuse reflection capacity (reflectivity) of the detection layer or a sensitive current or voltage measurement circuit for generating a measurement signal R from which the sought concentration C can be determined.

The test carriers are usually specifically suited to a particular analysis, i.e. one type of test carrier is used for determining the concentration of a particular component of a body fluid which is designated as "parameter". For a particular type of test carrier, for example for the analysis of glucose or cholesterol in blood, there is a particular relationship between the measurement signal R and the concentration C. The latter is termed the evaluation curve.

There is a problem here, however, which has been known since the early days of quantitative analysis by means of test carriers, namely that the test carriers are produced in batches, and it is usually not possible to make the manufacturing process so precisely reproducible that even with high requirements as to accuracy of the analysis the same evaluation curve can be used for different manufacturing batches. There have been several attempts to solve this problem.

The simplest solution is to dispense with a batch-specific correction. Even today test carrier analysis systems are still supplied in which a mean evaluation curve has been programmed into the evaluator, with allowance being made for the inaccuracies which this necessarily involves. It must be borne in mind that in most cases, by virtue of physical-chemical laws, the signal range, i.e. the total variation of the physical test value in the medically relevant measuring range, is comparatively small. As a result, even comparatively small errors in the evaluation curve lead to major differences in the measured concentration C.

A second method is calibration by means of calibration fluids of known concentration. With systems operating according to this system, a mean evaluation curve is also stored in the evaluator, which can however be corrected in individual cases by means of calibration measurements. This method is however time-consuming and complicated, and increasingly so the greater the desired accuracy is. In most cases, in fact, it is not sufficient to calibrate only with a single concentration if good accuracy over the whole measuring range is the goal. This method is therefore rather unsuitable particularly with analysis systems which are designed for use by lay persons (so-called "home monitoring").

In order to avoid these problems, several solutions have been proposed in which the information required for making use of the batch-specific evaluation curve is conveyed to the evaluator and used by the latter for the conversion of the measurement signal R into the concentration C.

One of the very first systems for analysing glucose, which worked on the analog electronic principle, made use of the batch-specific evaluation curve by means of exchangeable graduated discs, which were incorporated in the respective test strip packages. In European patent application EP-A 0073056 (correponding to U.S. Pat. No. 4,592,893) a system is described; the test carriers of which possess a bar code which contains the batch-specific evaluation curve. The associated evaluator contains a bar code reader for recording the information. EP-A 132790 (corresponding to U.S. Pat. No. 4,578,716) is concerned with the storage of the information in a magnetic layer located on the test carriers. The evaluator has a corresponding magnetic reading head. In the system described in EP-A 247 439 the evaluator contains certain basic information on the batch-specific evaluation curve, namely a standard evaluation curve and calculation checkpoints. The instrument is thereby capable of generating a batch-specific evaluation curve which approximates very closely to the true evaluation curve if it is inputted with a three-digit number which leads to the selection of the particular calculation checkpoints to be used.

SUMMARY OF THE INVENTION

The object of the invention is to provide a test carrier analysis system which is similarly simple and hence cost-effective as systems without batch-specific correction and which nevertheless makes this correction possible. Ease and reliability of handling are also aimed at.

This object is achieved by the test carrier analysis system according to the invention, which comprises test carriers containing in one or more test layers reagents, in which the reaction of the reagents with the component leads to a physically detectable change in a detection layer, the change follows a particular relationship, obeying an evaluation curve, to the concentration of the component and the evaluation curve is dependent on the manufacturing batch of the test carrier, an evaluator containing a measurement and digitization circuit for measuring the physically detectable change, generating a measurement signal R and converting the measurement signal R into an intermediate result independent of the evaluation curve by digitization of the measurement signal R into a finite number of digital output states $X_i$ and a display for indicating the output states in the form of an alphanumeric code and a readable information carrier element with a correlation between the alphanumeric codes of the display corresponding to the discrete output states $X_i$ and end result values determined by means of the evaluation curve. The end result values are preferably concentration values of the component to be determined. They can however also be other items of information derived from the analysis result.

The advantages obtained with the invention relate to each of the three elements of the system:

No special outlay has to be expended in the manufacture of the test carriers in order to manufacture the various production batches as uniform as possible. It is not even necessary for the evaluation curve to have the same general shape.

The evaluator can be of extremely simple design. In the simplest version it comprises—in addition to basic elements such as a power supply and the unit for recording the physically detectable change (for example measurement optics)—only a measuring amplifier and a digitization circuit. In particular a microprocessor with associated memory chips is not required.

Despite this simple design, not only is a single evaluator suitable for the evaluation of one type of test carriers, but different test carriers can be evaluated for different parameters with the same evaluator. It is not even necessary for the specific properties of future test carriers to be known in detail at the time of manufacture of the evaluator, provided they are consistent with the evaluator as regards the measurement principle, i.e. the physically detectable change, and naturally as regards the external design.

There can be used as information carrier element simply the package of the test carriers. It may also be appropriate, however, to attach to the test carriers a special evaluation card or to provide the correlation between the codes of the display and the concentration values on the test carriers themselves (for example on the back) in order to preclude the risk of any confusion.

BRIEF DESCRIPTION OF THE DRAWINGS

The invention will be explained in detail below with reference to an exemplifying embodiment shown diagrammatically in the figures, where.

DETAILED DESCRIPTION OF THE PREFERRED EMBODIMENT

Figure 1A:
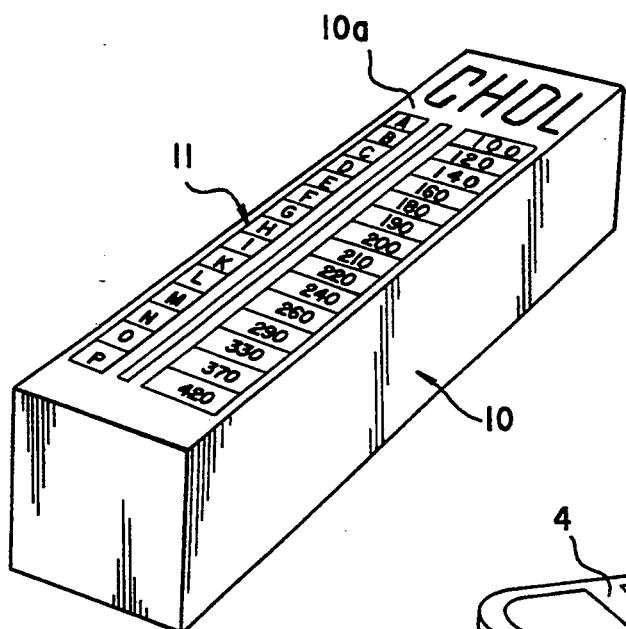
FIG. 1 is a test carrier analysis system according to the invention in perspective view.
Figure 1B:
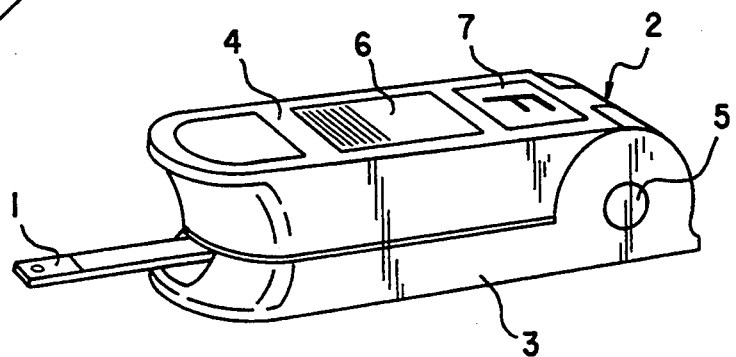

The test carrier 1 represented in FIG. 1 is inserted into an evaluator 2. In the represented case the evaluator 2 consists of a bottom part 3 and a top part 4 which are connected to each other by a hinge 5.

The top part 4 can be folded back in order to accomodate the test carrier 1. This particularly small and appropriate design, in which the whole unit serves as a support for the test carrier, is made possible by the fact that the evaluation electronics can be miniaturized on an extremely small scale according to the invention. The overall size of the unit when installed is determined mainly by the mechanical measures required to accomodate the test carrier.

On the top side of the unit is located next to a battery compartment 6 a display 7 which indicates an alphanumeric code (in the figure the letter F). This code is visually readable and has a comparatively small number of discrete states for indicating an intermediate result independent of the evaluation curve. The letters of the alphabet are for example suitable as the code.

The number of states of the display indication should in general be relatively small. A maximum of 40 states is preferable, 10 to 30 particularly preferable. Instead of the represented letter display, another easily readable display can also be provided, in particular a two-figure number.

A test carrier package 10 serves as information carrier element. It contains the correlation between the alphanumeric codes of the display 7 and the associated concentration values in the form of a table 11 which in the represented case is printed onto a lateral face 10a of the test carrier package 10.

Figure 2:
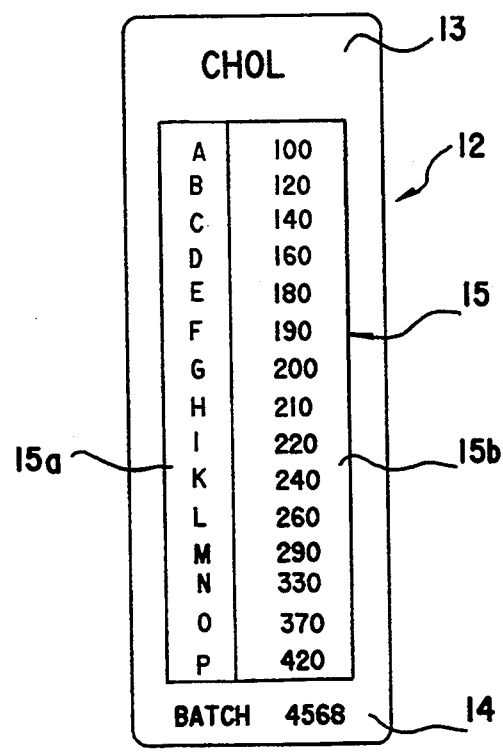
FIG. 2 is an adapted information carrier element.

FIG. 2 shows as a further example of a suitable information carrier element an evaluation card 12. The information carrier element is supplied by the manufacturer of the test carriers for evaluating a particular batch of a particular test carrier type. Accordingly it contains details of the parameter to be determined (in this case the code CHOL for cholesterol, parameter field 13) and the batch number (batch field 14).

The correlation table 15 makes use of the batch-specific evaluation curve. Consequently the concentration value in the concentration column 15b, which is correlated with a particular alphanumeric code in the code column 15a, is dependent on the respective manufacturing batch. Whereas for one batch, for example, a concentration of 190 mmol/l is—as represented—correlated with the code F, a concentration value of 180 or 200 mmol/l can be correlated with the same code for another batch. The invention is directed not to any particular correlation or mathematical method suitable for its determination, but to the problem solution defined in the claims, which leads to a test carrier evaluation system of extremely simple design with simultaneous universal applicability and high accuracy.

Instead of the concentration values the correlation table can also indicate the analysis result in another form, for example by sub-division into areas ("reduced—normal—increased sharply increased").

Figure 3:
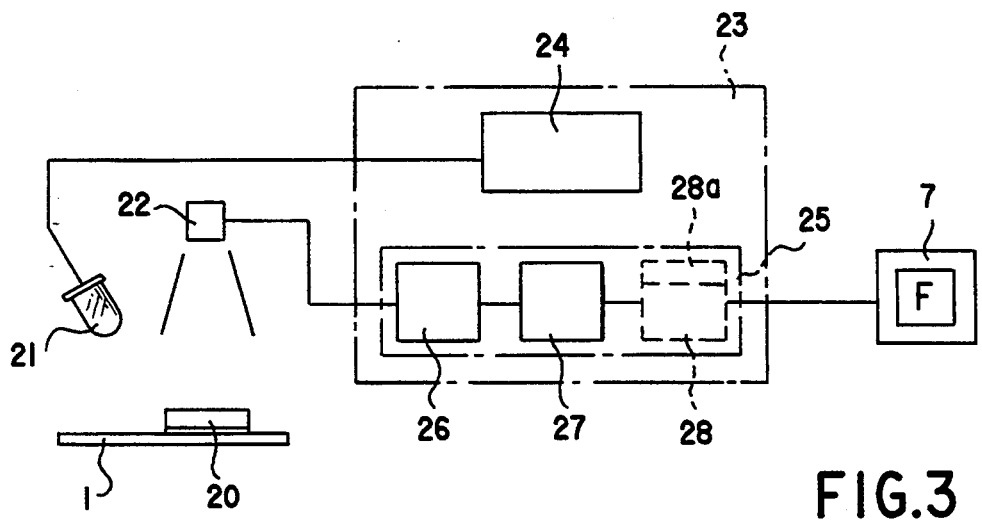
FIG. 3 is a block diagram of an evaluator for a system according to the invention.

FIG. 3 shows the main elements of an evaluator suitable for the invention in diagram form and as a block diagram.

In the represented case the diffuse reflection of the detection layer 20 of a test carrier 1 is to be determined. It is illuminated by a light emitting diode serving as light transmitter 21. The diffusely reflected light is collected by a light receiver 22, for example a phototransistor.

An electronic assembly designated overall as 23 contains a light transmitter control unit 24 and a measurement and digitization circuit 25 which incorporates a measuring amplifier 26, a digitization circuit 27 and a signal processing circuit 28 which is optional and hence drawn in broken lines. The output signal of the measurement and digitization circuit 25 appears on the display 7.

The measurement signal generated by the light receiver 22 is in the simplest case merely amplified by the amplifier 26, digitized by the digitization circuit 27 into one of a comparatively small number of output states of the measurement and digitization circuit 25 and indicated as an intermediate result on the display 7. The correlation between the output states and the concentration values is contained on the visually readable code carrier element. The evaluator itself therefore needs neither the information on the batch-specific evaluation curve nor expensive electronic components in order to determine from the measurement signals the concentration values in accordance with this evaluation curve.

It is not however intended to thereby exclude the possibility of the electronic assembly 23 containing other signal processing components, which are symbolised in FIG. 3 by the signal processing circuit 28.

It may in particular be advisable to use as digitization circuit a component obtainable commercially for this purpose, by means of which the measurement signal is digitized into one of a plurality of states (for example 256 states). The signal processing circuit contains in such a case logic devices which sub-divide the total number of states at the output of the digitization circuit into a number of sub-areas which correspond in each case to a state of the alphanumeric code.

In general terms the measurement and digitization circuit 25 sets discriminator thresholds by means of which the states of the alphanumeric code are correlated with the value range of the measurement signal. This relation does not have to be linear, i.e. the signal difference of the measurement signal in which a certain output signal of the measurement and digitization circuit 25 is generated-does not have to be the same for every state of the code. Instead it is frequently expedient to deliberately choose a non-linear relationship.

For example, the measurement signal curves frequently have in practice a sharply curved shape, and it may be expedient to linearize them. It may also be advantageous to spread the signal curve shape in the region interesting from a medical viewpoint with electronic means in order thereby to achieve an improved resolution of the concentration values in this region. This can be achieved in a simple manner by the discriminator thresholds for the output states lying in this region being brought closer together than those in the regions less interesting medically.

Figure 4:
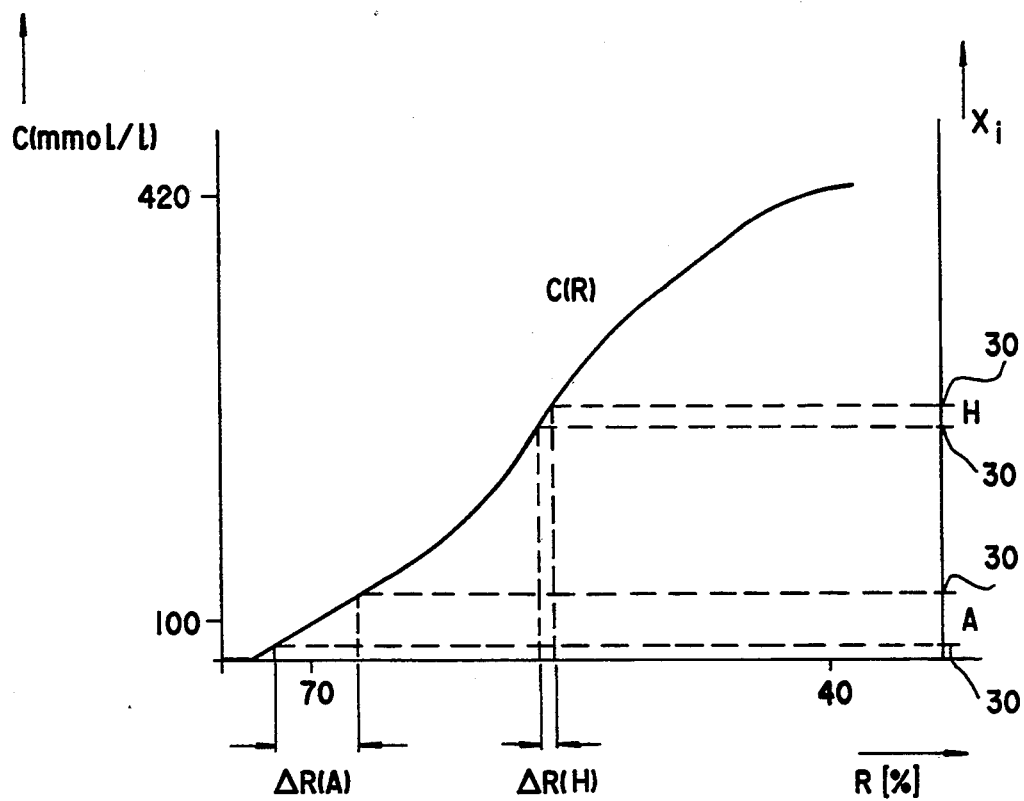
FIG. 4 is a graph in explanation of a preferred embodiment.

These preferred measures can be explained with reference to FIG. 4. The latter shows an evaluation curve C (R), i.e. the plot of a concentration (here expressed in mmol/l) versus the measured value R (here the reflectivity of a test layer at a particular wavelength, expressed in %). It will be seen that the whole of the medically interesting value range of 100 to 420 mmol/l corresponds the only a relatively small reflectance range of 70 to 40%. Moreover it is disadvantageous that in the medium concentration range, which is the most interesting one, the evaluation curve rises comparatively steeply, i.e. a large change in C corresponds to only a comparatively small change in R.

In such a case the accuracy of the evaluation will be improved if the discriminator thresholds 30, some of which are included as examples in the figure on the right-hand ordinate, are in the medium value range set comparatively close together and in the edge areas far apart. In other words, in the medically most interesting area an output state (in the represented case the state H) is correlated with a comparatively small measurement signal difference, $\Delta R$, whereas in the edge areas a comparatively broad section $\Delta R$ (A) of the total measuring rang corresponds to an output state (here A).

The invention also permits a particularly simple correction of the temperature influence. A temperature sensor 28a is provided for this purpose, the measurement result of which influences the signal processing. The simplest way in which this can occur is for the output states of the measurement and digitization circuit to be raised or lowered respectively to the next adjacent state if the temperature changes by a particular amount (e.g. 3° C. or 5° C.).

The skilled man is familiar with the means for the technical implementation of these preferred measures. The signal processing preferably takes place in digital form, for example as explained above by means of a conventional digitization circuit and a subsequent logic device. In this case the signal processing circuit is—as represented—situated in the signal path behind the digitization circuit.

If the signal processing is to take place with analog electronic means, it may however also be expedient to provide them in the signal path between measuring amplifier and digitization circuit. Finally, a special digitization circuit is also possible which incorporates the signal processing function.

As mentioned, the evaluator receives in the case of the present invention no information of any kind on the batch-specific evaluation curve. It is consequently also not possible to select the discriminator thresholds for the states of the measurement and evaluation circuit in such a way that an alpha-numeric code corresponds in each case to a round concentration value. In practice it is nevertheless usually sufficient to assign, on the information carrier element, the nearest round concentration value to the respective code, as illustrated in FIGS. 1 and 2.

The signal processing circuit can in the case of an evaluator suitable for the evaluation of several parameters also be used to mutually approximate the various curve shapes of the measurement signal in the respective measuring range, in order to distribute the possible states of the display uniformly over the whole measuring range and thus enable the most accurate evaluation possible to be achieved. If for example the signal curve with a test carrier for glucose is comparatively steep, while a cholesterol test carrier has only a small signal range, it is advisable to spread the cholesterol signal by means of the signal processing circuit until its whole range matches that of the glucose signal. To this end the evaluator must naturally be supplied with or contain relevant information on the type of test carrier to be evaluated and on the general shape of the respective evaluation curve. With such an embodiment also, however, the total outlay is still small compared with a currently known multi-parameter unit.

I claim:

1. A test carrier analysis system for analyzing a component of a fluid sample comprising:
    a plurality of test carriers containing at least one reagent in at least one test layer thereof, in which a reaction of the at least one reagent with a component to be analyzed leads to a detectable change in at least one of said test layers, wherein the detectable change follows a particular relationship, obeying an evaluation curve wherein a parameter of the fluid sample corresponds to the detectable change of the concentration of the component, and wherein the evaluation curve is dependent on a manufacturing batch of the plurality of test carriers;
    evaluation means for evaluating a test carrier which has undergone said detectable change comprising a measurement and digitization circuit for (a) measuring said physically detectable change, (b) generating a measurement signal and (c) converting the measurement signal into an intermediate result independent of the evaluation curve by digitization of the measurement signal into one of a finite number of digital output states;

display means for displaying the one of the finite number of digital output states in the form of alpha and/or numeric characters; and a readable information carrier element associated with each test carrier or with each plurality of test carriers providing a correlation between the alpha and/or numeric characters corresponding to said digital output states and end result values determined in accordance with the evaluation curve, wherein said end result values correspond to a parameter of the component of the fluid sample, said readable information carrier element is specifically made for each test carrier manufacturing batch, and wherein the correlation of the alpha and/or numeric characters to the end result values may be different from batch to batch.

2. A test carrier analysis system according to claim 1, wherein the finite number of digital output states of the measurement and digitization circuit is less than 40.

3. A test carrier analysis system according to claim 1, wherein the finite number of digital output states of the measurement and digitization circuit is between 10 and 30.

4. A test carrier analysis system according to claim 1, wherein said measurement and digitization circuit further comprises means for assigning varying measurement signal differences to the finite number of digital output states of the measurement and digitization circuit in different parts of a value range of said measurement signal.

5. A method for analyzing a fluid sample to determine the concentration of a component of the fluid sample, comprising the steps of:

contacting a fluid sample with a test carrier containing at least one reagent in at least one test layer thereof to cause a reaction between said at least one reagent and a component of the fluid sample to produce a detectable change in said at least one test layer, wherein the detectable change follows a particular relationship, obeying an evaluation curve wherein a parameter of the fluid sample corresponds to the detectable change, of the concentration of the component of the fluid sample, and wherein the evaluation curve may vary with different manufacturing batch lots of the test carrier;

evaluating a test carrier which has undergone said detectable change by (a) providing a device for measuring said detectable change, (b) measuring said detectable change, (c) generating a measurement signal, and (d) converting the measurement signal into an intermediate result independent of the evaluation curve by digitization of the measurement signal into one of a finite number of digital output states;

displaying the one of the finite number of digital output states in the form of alpha and/or numeric characters corresponding to said finite number of digital output states for correlation with end result values determined in accordance with the evaluation curve, said end result values corresponding to the concentration of the component of the fluid sample;

providing a readable information carrier element associated with the test carrier providing a correlation between said alpha and/or numeric characters corresponding to said digital output states and said end result values determined in accordance with the evaluation curve, said readable information carrier element being specifically made for each manufacturing batch lots of the test carrier, wherein said correlation of the alpha and/or numeric characters to the end result values may be different from batch to batch; and correlating said alpha and/or numeric characters with said end result values on said readable information carrier element to thereby determine the concentration of the component of the fluid sample.

6. A method for analyzing a fluid sample according to claim 5, wherein the finite number of digital output states is less than 40.

7. A method for analyzing a fluid sample according to claim 5, wherein the finite number of digital output states is between 10 and 30.

8. A method for analyzing a fluid sample according to claim 5, wherein the step of evaluating a test carrier further comprises assigning varying measurement signal differences to the finite number of digital output states in different parts of a value range of said measurement signal.

9. A method for analyzing a fluid sample according to claim 5, wherein said fluid sample comprises a body fluid.

10. A system for analyzing a fluid sample to determine the concentration of a component of the fluid sample, comprising:

a plurality of test carriers each containing at least one reagent in at least one test layer thereof;

an evaluation means for evaluating said plurality of test carriers, wherein upon contacting one of said test carriers with a fluid sample, a reaction occurs between said at least one reagent and a component of the fluid sample to produce a detectable change, said evaluation means evaluating said detectable change;

measuring means coupled to said evaluation means for measuring the physically detectable change;

generating means coupled to said measuring means for generating a measurement signal in response to said physically detectable change;

converting means coupled to said generating means for converting said measurement signal into an intermediate result, said intermediate result being independent of an evaluation curve of said plurality of test carriers;

display means for displaying an alpha and/or numeric character which corresponds to said intermediate result; and a readable information carrier element corresponding to each of said plurality of test carriers, said readable information carrier element including information which correlates said alpha and/or numeric characters and end result values corresponding thereto, said end result values corresponding to concentrations of the component of the fluid sample.

* * * * *